(12) United States Patent
Poulter

(10) Patent No.: US 11,364,040 B2
(45) Date of Patent: Jun. 21, 2022

(54) SURGICAL BURRING TOOL

(71) Applicant: Warsaw Orthopedic, Inc., Warsaw, IN (US)

(72) Inventor: Gregory Poulter, Zionsville, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 16/932,733

(22) Filed: Jul. 18, 2020

(65) Prior Publication Data

US 2021/0015495 A1    Jan. 21, 2021

Related U.S. Application Data

(60) Provisional application No. 62/875,751, filed on Jul. 18, 2019.

(51) Int. Cl.
*A61B 17/16* (2006.01)

(52) U.S. Cl.
CPC ...... *A61B 17/1671* (2013.01); *A61B 17/1617* (2013.01)

(58) Field of Classification Search
CPC . A61B 17/1671; A61B 17/1617; A61B 17/15; A61B 17/1757
See application file for complete search history.

(56) References Cited

U.S. PATENT DOCUMENTS

| | | | |
|---|---|---|---|
| 6,402,757 B1* | 6/2002 | Moore, III | A61B 17/862 606/104 |
| 2009/0048602 A1* | 2/2009 | O'Donoghue | A61B 17/1615 606/80 |
| 2010/0292700 A1* | 11/2010 | Ries | A61B 17/1615 606/80 |
| 2011/0082555 A1* | 4/2011 | Martz | A61F 2/4611 623/17.16 |
| 2011/0319941 A1* | 12/2011 | Bar | A61B 90/11 606/279 |
| 2015/0313615 A1* | 11/2015 | Jacobson | A61B 17/1615 606/85 |
| 2015/0342621 A1* | 12/2015 | Jackson, III | A61B 1/3135 600/546 |

* cited by examiner

*Primary Examiner* — Zade Coley
*Assistant Examiner* — Diana Jones
(74) *Attorney, Agent, or Firm* — Sorell, Lenna & Schmidt, LLP

(57) ABSTRACT

An orthopedic burring tool includes a burring tip configured for removal of bone to form a bore in the bone, an elongated intermediate segment having a smooth outer surface along a length of the segment, a conical widening segment at the proximal end of the intermediate segment that widens from the diameter of the burring tip to a diameter that is about twice the burring tip diameter. The widening segment includes an outer surface configured for removal of bone upon rotation of the burring tool. The tool includes an upper segment configured for engagement to a rotary driving tool and having a cylindrical outer surface configured for removal of bone upon rotation of the burring tool for removal of material from bony structure adjacent the bone bore formed by the burring tip.

19 Claims, 3 Drawing Sheets

SURGICAL BURRING TOOL

PRIORITY CLAIM

This application is a utility filing of and claims priority to U.S. provisional application No. 62/875,751, filed on Jul. 18, 2019, the entire disclosure of which is incorporated herein by reference.

BACKGROUND

Spinal fixation systems rely on anchoring stabilization components to the vertebral body. In one approach, the stabilization components are anchored by bone screws or bolts introduced into the vertebral body, such as along the pedicle. In a common procedure, the vertebral bone is prepared for the introduction of the bone screw by drilling a bore into the vertebral body and then threading the screw or bolt BT into that bore, as shown in FIGS. 3A-3B. A burring tool is used to prepare the bore. Burr guides are often used to ensure that the burring tool is advanced on a proper line into the vertebral body. This is a particularly important consideration in preparing a bore through the pedicle to ensure that the bore is solidly contained within the pedicle and that the bore does not deviate from the pedicle into the vertebral foramen.

In addition, in many fixation installations, the bone screw/bolt BT includes a "tulip" head TL configured to receive an elongated spinal rod, as shown in FIGS. 3A-3B. The spinal rod is bent to a desired contour so that the patient's spine adopts the desired contour when the spinal rod is anchored to the spine. The tulip head TL receives a locking screw L to lock the rod to the bone screw/bolt BT. The tulip head includes a generally spherical bottom surface S that contacts the vertebral bone when the bone screw/bolt is fully engaged within the vertebral body. Thus, in addition to preparing the opening using a burring tool, an additional tool is often used to contour the surface of the bone to receive the tulip head of the bones screw/bolt. However, since a different tool is used to contour the bone surface, in some instances the surface contouring can deviate from the path of the bore so that the contoured surface does not accept the tulip head of the bone screw when it is introduced into the bore.

In addition, in order to permit the bone screw to be advanced into the prepared bore, it is often necessary to remove bone adjacent to the insertion site. Thus, yet another burring tool is often used to remove bone from the facet joint F or transverse process TP that might be along the axis of introduction of the bone screw/bolt.

There is a need for a tool that can prepare the entire site for introduction of a bone bolt, without the need to use separate tools. There is also a need for a tool that can ensure proper orientation of the prepared bone surface with a bore formed in the bone.

SUMMARY OF THE DISCLOSURE

An orthopaedic burring tool includes an elongated intermediate segment having a smooth outer surface along a length of the intermediate segment and a burring tip connected to the distal end of the intermediate segment. The burring tip has an outer surface configured to remove bone upon rotation of the burring tool to form a bore in the bone. The tool further includes a conical widening segment connected to the proximal end of the intermediate segment. The widening segment increases in diameter from the diameter of the burring tip to a larger diameter at the proximal end of the widening segment that can be about twice the diameter of the burring tip. The widening segment has an outer surface configured for removal of bone upon rotation of the burring tool.

The burring tool further includes an upper segment configured for engagement to a rotary driving tool and connected to the proximal end of the widening segment. The upper segment is cylindrical and has a diameter greater than largest diameter of the widening segment. The upper segment has a cylindrical outer surface configured for removal of bone upon rotation of the burring tool to remove material from a bony structure adjacent the site of introduction of the burring tool into the bone. When the burring tool is used to prepare a pedicle of a vertebra for introduction of a bone screw/bolt, the burring tip creates the bore and the widening segment creates a funnel-shaped opening for the bore to receive the distal surface of the tulip head of the bone bolt. The upper segment removes material from an adjacent bony structure to provide clearance for introduction of the pedicle screw.

DETAILED DESCRIPTION

Figure 1:
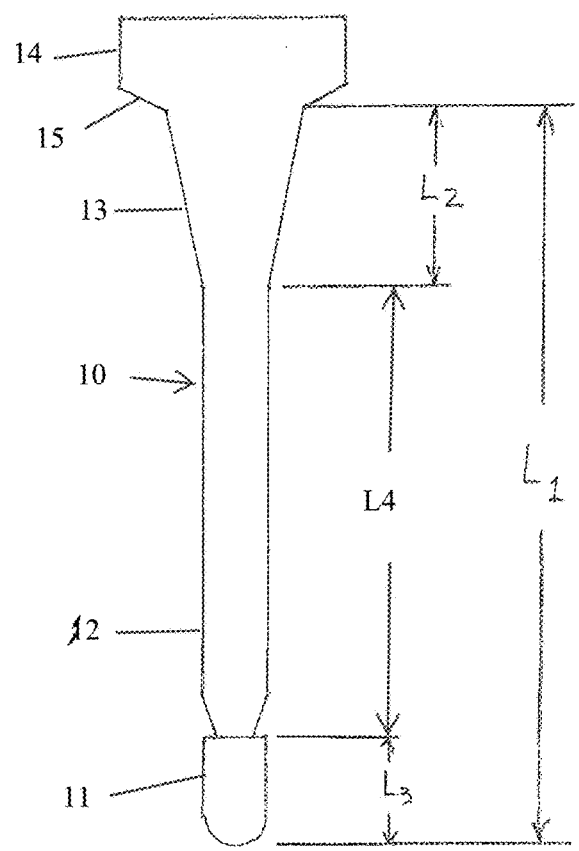
FIG. 1 is a side view of a burring tool according to one embodiment of the present disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

The present disclosure provides a burring tool that ensures alignment of the surface contour with the bone screw bore and that automatically prepares adjacent bone for introduction of the bone screw/bolt BT. As shown in FIG. 1, the burring tool 10 includes a burring tip 11 that can be configured like a conventional burring tool for spinal surgical applications. In particular, the burring tip can include a series of helical or spiral cutting flutes around the circumference of the tip. The burring tip 11 is integral with the distal end of an elongated smooth intermediate segment 12, with the smooth shaft having the same outer diameter as the burring tip. In one specific embodiment, the outer diameter is 3 mm to prepare a bore for receiving a conventionally sized bone screw or bolt. In one specific embodiment, the burring tip 11 has a length L3 of about 3 mm and the smooth intermediate segment 12 has a length L4 of about 15 mm.

The proximal end of the smooth intermediate segment 12 is integral with a conical widening segment 13 in which the diameter of the tool 10 gradually increases from the diameter of the burring tip at the distal end of the widening segment to a diameter at the opposite proximal end of the segment that is sized to receive the intermediate portion of the bone screw/bolt and the base of the tulip head of the bolt/screw. In one specific embodiment, the widening segment 13 is configured to remove bone and in particular to widen the opening in the bone from the 3 mm of the burring tip to about 6 mm. The widening segment 13 has a length L2, which can be about 10 mm and subtends a conical angle of about 15-25 degrees in one specific embodiment. The overall length L1 of the bone bore preparing surfaces 11, 12, 13 of the burring tool 10 can be 28-30 mm in specific embodiments for the preparation of a bore in the pedicle of a lumbar vertebral body. Other overall lengths L1 are contemplated depending on the vertebral level being prepared. The average pedicle length for the L5 vertebra is about 24 mm, but can vary ±7 mm, so different overall lengths L1 are necessary. The pedicle lengths of the thoracic vertebrae range from 4.5 mm at T4 to 10 mm at T12, so again different overall lengths L1 are dictated. Likewise, for the cervical spine.

The burring tool 10 terminates in an upper segment 14 integral with the widening segment 13 by a transition segment 15. The upper segment is generally cylindrical and has a larger outer diameter than the remainder of the burring tool 10 because the upper segment 14 is arranged to remove material from bony structure adjacent the insertion site of the bone screw/bolt. Thus, in one specific embodiment, the upper segment 14 has a diameter of 10 mm and a length of about 5 mm. The transition segment 15 is thus configured to transition between the two diameters and is preferably conical over a length of 1-2 mm. Like the burring tip 11 and the widening segment 13, the upper segment 14 is configured to remove bone.

The upper segment 14 is configured to be mounted to a rotary driving tool for high-speed rotation of the burring tool. Thus, the upper segment can include a threaded bore or a projecting stem configured to engage a rotary driving tool in a known manner. It is contemplated that the burring tool can include a central bore along its length for introduction of the tool along a guide wire or K-wire to ensure that the bore is prepared at the proper angle within the vertebral body.

The diameters of the bone removing surfaces can be modified as needed based on location of the bone bore being created. The first diameter—the diameter of the burring tip—can be equal to a second diameter—the smaller diameter of the widening segment. A third diameter—the larger diameter of the widening segment—can be twice the first diameter. A fourth diameter—the diameter of the cylindrical upper segment—can be at least three times the first diameter.

Figure 2A:
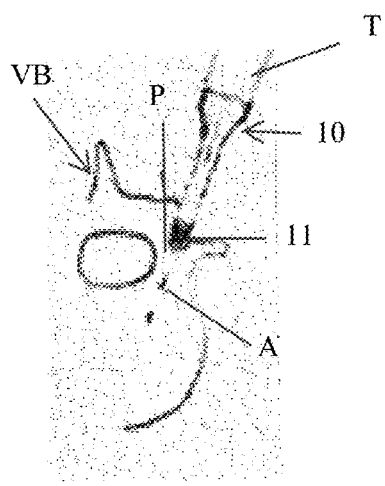
FIGS. 2A-2C a view in the transverse plane of a vertebral body showing successive steps of the introduction of the burring tool shown in FIG. 1 into the pedicle of the vertebra.
Figure 2B:
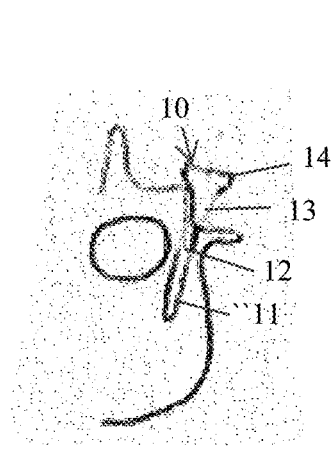
Figure 2C:
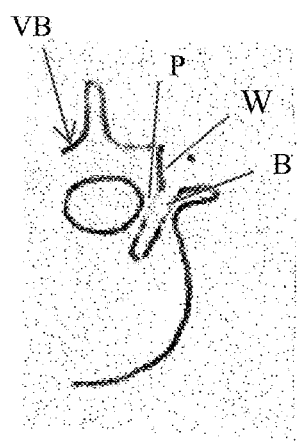

Use of the burring tool 10 is depicted in FIGS. 2A-2C. In the initial step, the burring tool 10, mounted on a driving tool T, is introduced along a desired bore axis A through the pedicle P of a vertebral body VB. The tool 10 is advanced along the axis A into the bone until the upper segment 14 contacts the adjacent bony structure, as shown in FIG. 2B. As the burring tool is advanced further into the vertebral body VB, the upper segment removes material from the adjacent bony structure, providing a clear path for introduction of the bone screw/bolt, as shown in FIG. 2C. As the burring tool is advanced along the bore axis A, the burring tip 11 creates a path for the tool 10 through the bone. The small burring tip is advantageous for providing a precise starting point and trajectory for the bore axis A with minimal deflection of the tool, even at high introduction angles. In conventional approaches, as the burring tool is advanced further into the bone the tool tends to deflect or deviate from the desired path. The tool 10 of the present disclosure avoids that problem with the smooth intermediate segment 12 which contacts the wall of the newly-prepared bore created by the burring tip. Since the intermediate segment 12 is smooth it does not impede the advancement of the tool into the bone as the burring tip 11 is driven further into the bone. Instead, the intermediate tip acts as a bearing surface or burr guide to maintain the proper orientation of the burring tool 10 and to prevent deflection of the tool as the tip moves deeper into the bone.

Figure 3A:
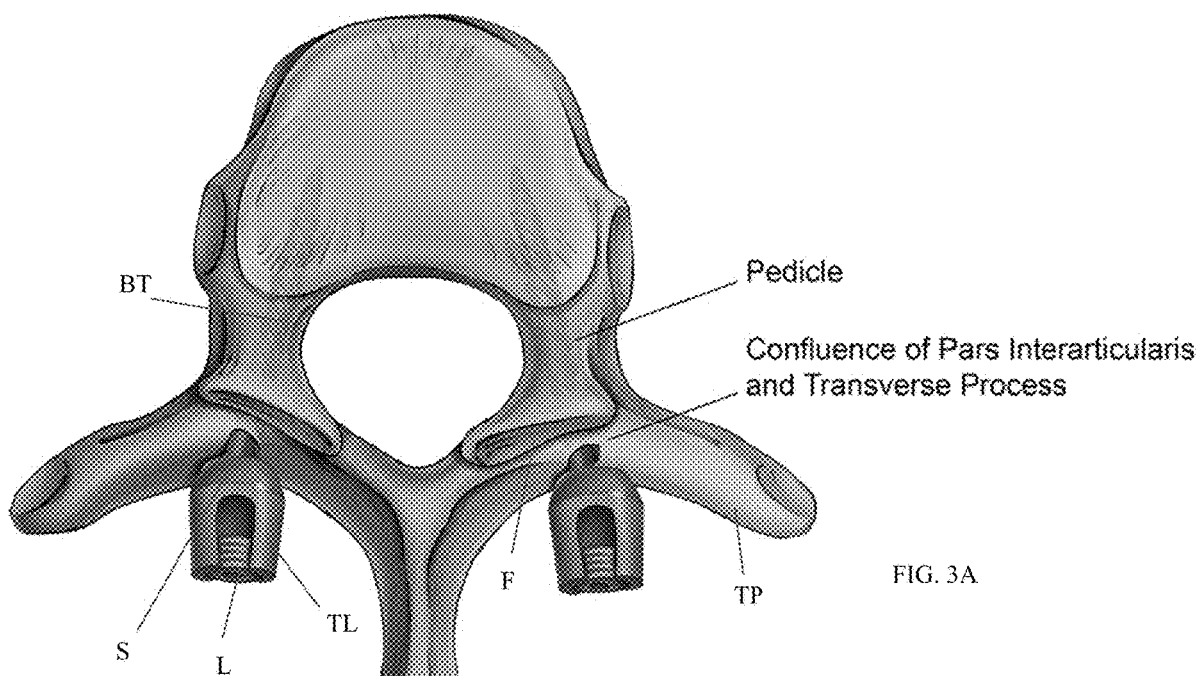
FIGS. 3A-3B are views in the transverse and sagittal planes of a lumbar vertebra with a bone bolt placed in the pedicles of the vertebra.
Figure 3B:
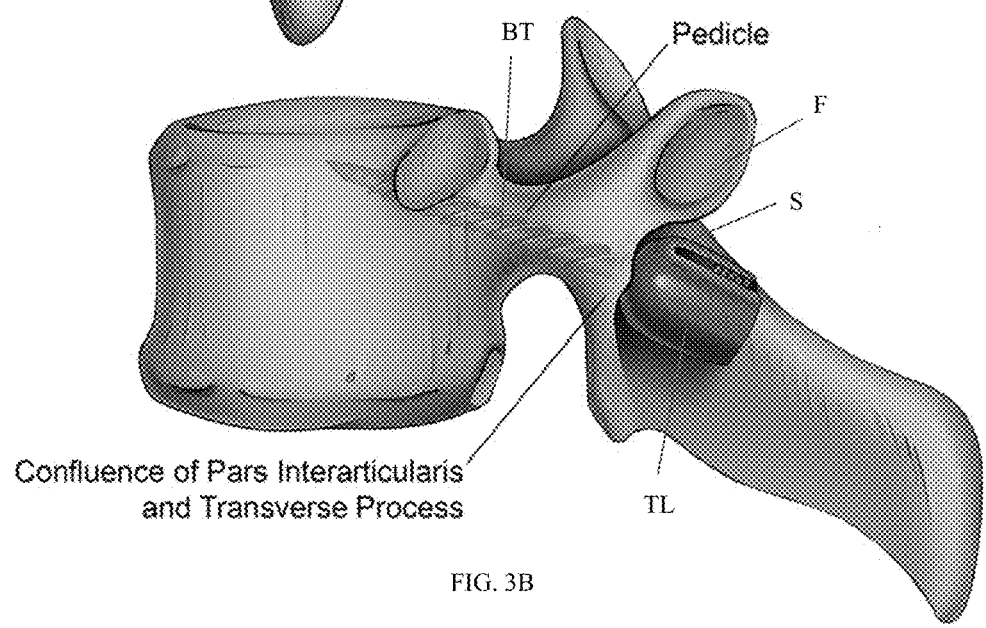

Eventually the widening segment 13 contacts the bone and begins to enlarge the upper portion of the bore B in the bone, as depicted in FIG. 2C. The intermediate segment 12 helps maintain the proper alignment of the tool along the axis A even as the upper portion of the bore is being widened. After the burring tool has been advanced to the desired depth, the resulting bore B is configured to accept the bone screw/bolt with a widened funnel shaped portion W at the bone surface to accommodate the tulip head TL of the bone screw/bolt BT (FIG. 3A). The diameter of the widened portion W can be determined by the distal surface of the tulip head TP, and that diameter is ultimately determined by the depth that the burring tip 11 is introduced into the bone. After the burring tool has advanced to its desired depth to create the bore B, the upper segment 14 has removed adjacent bone, as shown in FIG. 2C so that the bone screw/bolt can be readily threaded into the prepared bore without interference from adjacent vertebral bony structure.

It is contemplated that the burring tool 10 is an integrally formed structure. However, it is also contemplated that the segments of the tool can be separate and engaged to each other to form the complete tool. Thus, two or more of the burring tip 11, intermediate segment 12, conical widening segment 13 and upper segment 14 can be separate components that can be combined to form the tool 10. It is contemplated, for instance, that different lengths of intermediate segments 12 can be provided for engagement with a common burring tip 11 depending on length of the bone bore to be created. Likewise, different lengths of widening segments 13 may be provided for use in a similar manner.

Figure 4A:
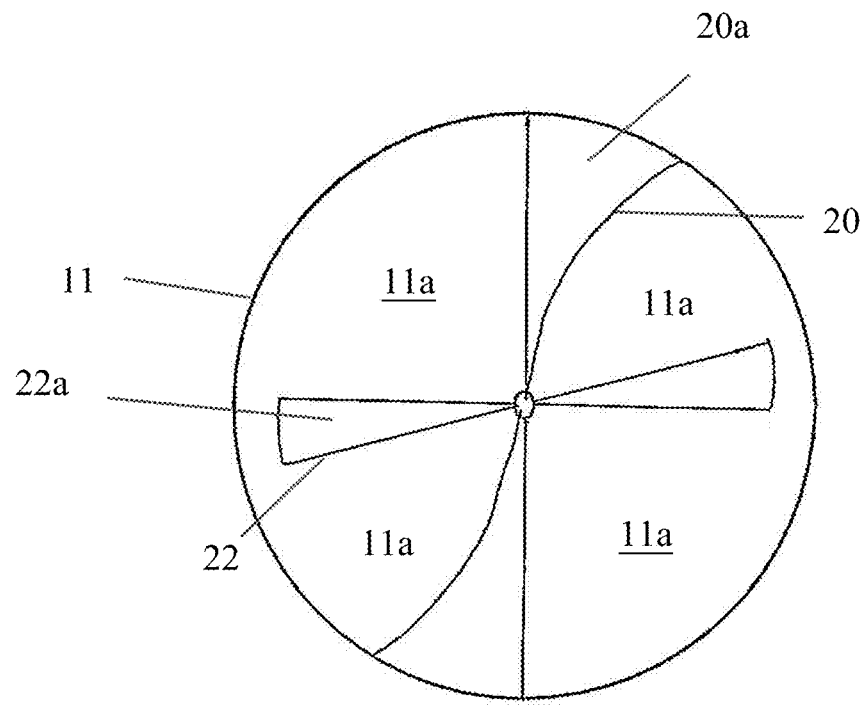
FIG. 4A is an end view of the burring tip of the burring tool shown in FIG. 1 and depicting the bi-directional cutting edges of the burring tip according to one embodiment of the disclosure.

As explained above, the tool 10 is configured to be driven by a rotary driving tool for high-speed rotation of the tool. In one embodiment, the tool is rotated in one direction during the process for preparing the bone bore. In another embodiment, the tool can be bi-directional, meaning that it can be rotated in either the clockwise or counter-clockwise directions. In this embodiment, one or more of the bone preparing surfaces 11, 13, and 14 can be configured for different bone removal characteristics depending upon the direction of rotation. Thus, in the conventional driving direction (clockwise), the surface is configured for rapid removal of bone, whereas in the opposite direction (counter-clockwise), the surface if configured for fine bone removal to produce a smooth prepared surface of the bone. This attribute can be particularly advantageous for the funnel-shaped portion W of the bone bore B which receives the distal surface S of the tulip head TL. In one embodiment, shown in FIG. 4A, the burring tip 11 can incorporate the bi-directional bone preparing surface. In a particular, the surface includes an aggressive cutting edge 20 that is curved to increase the length of the edge. The edge 20 is generally concave in the direction of rotation, which is clockwise as viewed in FIG. 4A. The edge 20 is defined by an inclined surface 20a that extends from the primary surface 11a of the burring tip. In a specific embodiment, the cutting edge 20 can project a height of 0.3 mm from the surface 11a. In the illustrated embodiment, the burring tip 11 is provided with two aggressive cutting edges 20 spaced 180° apart.

The burring tip includes a less aggressive cutting edge 22 that faces the other direction of rotation, which is counter-clockwise in the figure. The edge 22 is generally straight and indented from the outer edge of the burring tip 11. The edge 22 is at the end of an inclined surface 22a projecting from the primary surface 11a of the burring tip. In a specific embodiment, the less aggressive cutting edge can project a height of 0.2 mm from the surface 11a. In other embodiments, the less aggressive cutting edges can project a height above the primary surface that is ½-⅔ the height of the aggressive cutting edges. In the illustrated embodiment, two edges 22 are situated between the two aggressive cutting edges 20. It is understood that when the burring tool is rotated in the clockwise direction (as viewed in the figures), only the aggressive cutting edges 20 will remove material from the bone. When the burring tool is rotated in the opposite (counter-clockwise) direction, only the less aggressive cutting edges 22 will remove material from the bone. Since the cutting edges 22 are less prominent than the aggressive cutting edges 20, the material removed in a given full rotation in the counter-clockwise direction will be less than the material removed by the aggressive edges in a full clockwise rotation.

Figure 4B:
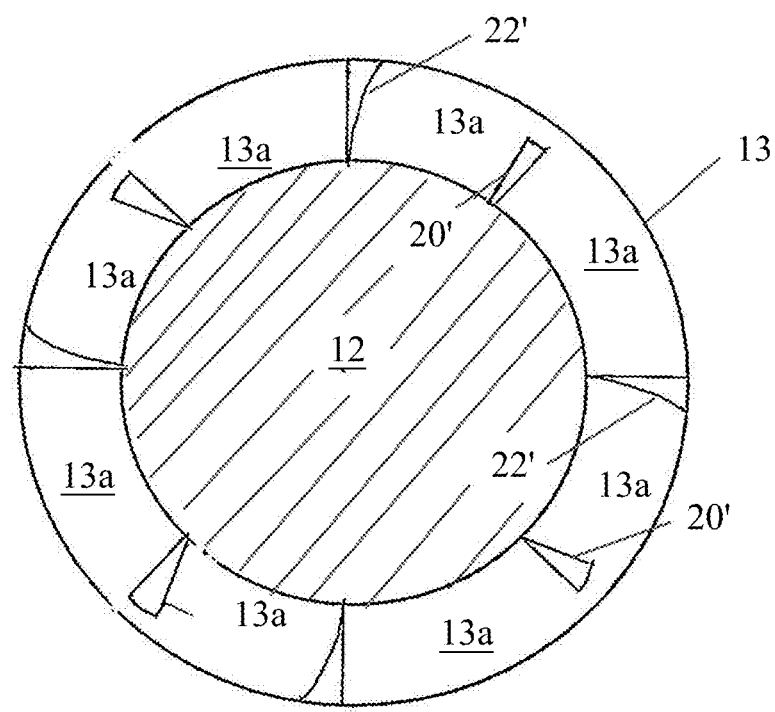
FIG. 4B is a partial cross-sectional view of the burring tool taken at the interface between the intermediate segment and the widening segment of the burring tool shown in FIG. 1 and depicting bi-directional cutting edges of the widening segment according to one embodiment of the disclosure.

The same principle can be applied at the surface 13a of the widening portion 13, as shown in FIG. 4B. Thus, the widening portion can include aggressive cutting edges 20' and less aggressive cutting edges 22' extending from the interface with the intermediate segment 12 to the interface with the transition segment 15. The edges 20' are configured in a similar manner to the edges 20, and the edges 22' are configured in a similar manner to the edges 22, so that greater bone material is removed for clockwise rotation (in the specific example) than is removed for counter-clockwise rotation. As noted above, the aggressive cutting edges 20' of the widening segment 13 can initially prepare the funnel-shaped portion W of the bone opening, followed by reverse rotation and use of the less aggressive cutting edges 22' to provide a smooth surface to the portion W to receive the tulip head of the bone bolt. In the embodiment shown in FIG. 4b, four cutting edges 20' and four cutting edges 22' are distributed uniformly around the circumference of the surface 13a. Other numbers of cutting edges are contemplated. The same cutting edge structure can be applied to the bone removing surface of the upper segment 14.

The present disclosure should be considered as illustrative and not restrictive in character. It is understood that only certain embodiments have been presented and that all changes, modifications and further applications that come within the spirit of the disclosure are desired to be protected.

What is claimed is:

1. An orthopedic burring tool comprising:
   an elongated intermediate segment having a smooth outer surface along a length of the intermediate segment from a proximal end to an opposite distal end, said intermediate segment defining a longitudinal axis along said length;
   a burring tip connected to said distal end of said intermediate segment and having an outer surface configured to remove bone upon rotation of the burring tool to form a bore, said burring tip having a first diameter;
   a conical widening segment connected at a distal end thereof to the proximal end of said intermediate segment, said widening segment having a second diameter at the distal end of the widening segment substantially equal to said first diameter and having a third diameter at an opposite proximal end of the widening segment that is larger than said first diameter, said widening segment having an outer surface configured for removal of bone upon rotation of the burring tool; and
   an upper segment configured for engagement to a rotary driving tool and connected to the proximal end of said widening segment, said upper segment being cylindrical and having a fourth diameter greater than said third diameter, said upper segment having a cylindrical outer surface configured for removal of bone upon rotation of the burring tool,
   wherein the outer surface of the widening segment includes two or more aggressive cutting edges oriented to remove material from bone in one direction of rotation of the burring tool, and two or more less aggressive cutting edges oriented to remove material from bone in an opposite direction of rotation of the burring tool.

2. The orthopedic burring tool of claim 1, wherein said upper segment is connected to said widening segment by a conical transition segment.

3. The orthopedic burring tool of claim 1, wherein said conical widening segment subtends a conical angle of 15-25 degrees.

4. The orthopedic burring tool of claim 1, wherein said first diameter is 3 mm.

5. The orthopedic burring tool of claim 4, wherein said third diameter is 6 mm.

6. The orthopedic burring tool of claim 5, wherein said fourth diameter is 10 mm.

7. The orthopedic burring tool of claim 1, wherein said third diameter is twice the first diameter.

8. The orthopedic burring tool of claim 7, wherein said fourth diameter is at least three times the first diameter.

9. The orthopedic burring tool of claim 1, wherein said fourth diameter is at least three times the first diameter.

10. The orthopedic burring tool of claim 1, wherein said burring tip has a length along said longitudinal axis of 3 mm.

11. The orthopedic burring tool of claim 1, wherein said intermediate segment has a length along said longitudinal axis of 15 mm.

12. The orthopedic burring tool of claim 1, wherein said widening segment has a length along said longitudinal axis of 10 mm.

13. The orthopedic burring tool of claim 1, wherein said upper segment has a length along said longitudinal axis of 5 mm.

14. The orthopedic burring tool of claim 1, wherein said burr tip, intermediate segment and widening segment have a combined length along said longitudinal axis of 28-30 mm.

15. The burring tool of claim 1, wherein the bone material removed by the less aggressive cutting edges in one full rotation in the opposite direction of rotation is less than the bone material removed by the aggressive cutting edges in one full rotation in the one direction of rotation.

16. The orthopedic burring tool of claim 1, wherein the less aggressive cutting edges are each positioned between adjacent ones of the aggressive cutting edges, the aggressive cutting edges being concavely curved, the less aggressive edges being straight.

17. An orthopedic burring tool comprising:
an intermediate segment extending along a longitudinal axis between a linear proximal end and an opposite tapered distal end;
a burring tip connected to the distal end and having a series of helical cutting flutes configured to remove bone upon rotation of the burring tool;
a widening segment connected to the proximal end, the widening segment including a plurality of aggressive cutting edges oriented to remove material from bone in one direction of rotation of the burring tool and a plurality of less aggressive cutting edges each positioned between adjacent ones of the aggressive cutting edges and oriented to remove material from bone in an opposite direction of rotation of the burring tool; wherein the aggressive cutting edges are concavely curved and the less aggressive edges are straight; and
an upper segment connected to the widening segment, the upper segment being cylindrical,
wherein the widening segment has a maximum length along the longitudinal axis that is greater than a maximum length of the tip along the longitudinal axis.

18. The orthopedic burring tool of claim 17, wherein:
the tip has a maximum diameter that is greater than a minimum diameter of the distal end;
the widening segment has a maximum diameter that is greater than a maximum diameter of the proximal end; and
the upper segment has a maximum diameter greater than the maximum diameter of the widening segment.

19. An orthopedic burring tool comprising:
an intermediate segment extending along a longitudinal axis between a linear proximal end and an opposite tapered distal end;
a burring tip connected to the distal end and having a plurality of first aggressive cutting edges oriented to remove material from bone in one direction of rotation of the burring tool and a plurality of first less aggressive cutting edges each positioned between adjacent ones of the first aggressive cutting edges and oriented to remove material from bone in an opposite direction of rotation of the burring tool, the first aggressive cutting edges being concavely curved, the first less aggressive edges being straight;
a conical widening segment connected to the proximal end, the widening segment including a plurality of second aggressive cutting edges oriented to remove material from bone in the one direction of rotation and a plurality of second less aggressive cutting edges each positioned between adjacent ones of the second aggressive cutting edges and oriented to remove material from bone in the opposite direction of rotation of the burring tool, the second aggressive cutting edges being concavely curved, the second less aggressive edges being straight; and
an upper segment connected to the widening segment, the upper segment being cylindrical and having a maximum diameter greater than the maximum diameter of the widening segment,
wherein the burring tool includes a central bore along its length for introduction of the burring tool along a guide wire.

* * * * *